US010912955B2

(12) United States Patent
Simon

(10) Patent No.: US 10,912,955 B2
(45) Date of Patent: *Feb. 9, 2021

(54) TREATMENT OF CELIAC DISEASE, C. DIFFICILE INFECTION, FOOD INTOLERANCE AND FOOD ALLERGY WITH SECRETORY IGA/IGM

(71) Applicant: Michael R. Simon, Ann Arbor, MI (US)

(72) Inventor: Michael R. Simon, Ann Arbor, MI (US)

( * ) Notice: Subject to any disclaimer, the term of this patent is extended or adjusted under 35 U.S.C. 154(b) by 563 days.

This patent is subject to a terminal disclaimer.

(21) Appl. No.: 15/205,359

(22) Filed: Jul. 8, 2016

(65) Prior Publication Data

US 2016/0319039 A1 Nov. 3, 2016

Related U.S. Application Data

(63) Continuation of application No. 15/014,200, filed on Feb. 3, 2016, now Pat. No. 9,409,996, which is a continuation of application No. 14/264,053, filed on Apr. 28, 2014, now Pat. No. 9,273,129, which is a continuation of application No. 13/214,952, filed on Aug. 22, 2011, now Pat. No. 8,709,413, which is a continuation-in-part of application No. 12/138,758, filed on Jun. 13, 2008, now Pat. No. 8,021,645, which is a continuation-in-part of application No. 11/851,606, filed on Sep. 7, 2007, now Pat. No. 7,794,721, which is a continuation-in-part of application No. 11/839,781, filed on Aug. 16, 2007, now Pat. No. 7,597,891, which is a continuation-in-part of application No. 11/610,154, filed on Dec. 13, 2006, now abandoned.

(51) Int. Cl.
| | |
|---|---|
| C07K 16/12 | (2006.01) |
| C07K 16/00 | (2006.01) |
| A61K 39/00 | (2006.01) |
| A61P 1/00 | (2006.01) |
| G06F 3/147 | (2006.01) |
| C07K 16/16 | (2006.01) |
| C07K 16/18 | (2006.01) |
| C07K 16/44 | (2006.01) |
| A61K 9/00 | (2006.01) |
| A61K 38/14 | (2006.01) |
| A61K 39/395 | (2006.01) |
| A61K 39/40 | (2006.01) |
| G02F 1/167 | (2019.01) |
| G02F 1/1333 | (2006.01) |

(52) U.S. Cl.
CPC .............. *A61P 1/00* (2018.01); *A61K 9/0053* (2013.01); *A61K 38/14* (2013.01); *A61K 39/39583* (2013.01); *A61K 39/40* (2013.01); *C07K 16/00* (2013.01); *C07K 16/1282* (2013.01); *C07K 16/16* (2013.01); *C07K 16/18* (2013.01); *C07K 16/44* (2013.01); *G06F 3/147* (2013.01); *A61K 2039/505* (2013.01); *A61K 2039/507* (2013.01); *A61K 2039/542* (2013.01); *A61K 2039/577* (2013.01); *C07K 2317/75* (2013.01); *C07K 2317/76* (2013.01); *G02F 1/167* (2013.01); *G02F 2001/133388* (2013.01); *G09G 2310/0232* (2013.01); *G09G 2340/04* (2013.01); *G09G 2340/0407* (2013.01); *G09G 2380/14* (2013.01)

(58) Field of Classification Search
None
See application file for complete search history.

(56) References Cited

U.S. PATENT DOCUMENTS

| | | | |
|---|---|---|---|
| 5,190,752 A | 3/1993 | Moller et al. | |
| 5,670,626 A | 9/1997 | Chang | |
| 5,773,000 A * | 6/1998 | Bostwick et al. | ......... 424/167.1 |
| 6,162,904 A | 12/2000 | Mamidi et al. | |
| 6,932,967 B2 * | 8/2005 | Simon | ........................ 424/130.1 |
| 6,967,106 B2 * | 11/2005 | Simon | ........................... 436/513 |
| 7,186,410 B2 | 3/2007 | Chtourou et al. | |
| 7,794,721 B2 | 9/2010 | Simon | |
| 8,021,645 B2 | 9/2011 | Simon et al. | |
| 8,709,413 B2 | 4/2014 | Simon | .................... C07K 16/16 |
| | | | 424/130.1 |
| 9,273,129 B2 | 3/2016 | Simon | .................... C07K 16/00 |

(Continued)

FOREIGN PATENT DOCUMENTS

| | | | | |
|---|---|---|---|---|
| WO | WO 2003/015817 | * | 2/2003 | ........... A61K 39/395 |
| WO | WO 2009/139624 A1 * | | 11/2009 | ............. C07K 16/04 |

OTHER PUBLICATIONS

Russell and Reynolds "Isolation and characterization of canine secretory immunglobulin M" J Immunol 1977: 118: 323-329 (Year: 1977).*
Levy et al. "Secretory anti-human immunodeficiency virus (HIV) antibodies in colostrum and breast milk are not a major determinant of the protection of early postnatal transmission of HIV" J. Infectious Diseases 2000; 181: 532-9 (Year: 2000).*
Doe "The intestinal immune system" Gut 1989, 30, 1679-1685 (Year: 1989).*

(Continued)

*Primary Examiner* — Daniel E Kolker
*Assistant Examiner* — James L Rogers
(74) *Attorney, Agent, or Firm* — Blue Filament Law PLLC

(57) ABSTRACT

A process is provided for inhibiting symptoms of celiac disease, *Clostridium difficile* associated diseases such as *Clostridium difficile* colitis, pseudomembranous colitis and antibiotic associated diarrhea, food allergy or food intolerance in a subject that includes the oral administration to the subject suffering from food allergy or food intolerance an IgM. When administered in a, therapeutic quantity based on the subject characteristics and the type of IgM, symptoms of food allergy or food intolerance in that subject are inhibited. Even non-secretory forms of IgM are effective when administered orally.

11 Claims, No Drawings

(56) References Cited

U.S. PATENT DOCUMENTS

| | | | |
|---|---|---|---|
| 2002/0012954 A1* | 1/2002 | Sirbasku | A61K 31/138 |
| | | | 435/7.23 |
| 2002/0110555 A1 | 8/2002 | Lee | |
| 2002/0114802 A1 | 8/2002 | Tjellstrom et al. | |
| 2004/0043019 A1 | 3/2004 | Joks et al. | |
| 2005/0058661 A1* | 3/2005 | Sykes | A61K 39/0225 |
| | | | 424/190.1 |

OTHER PUBLICATIONS

Casswall et al. 'Oral IgA-IgG treatment of chronic non-specific diarrhoea in infants and children.' Acta Pediatrica 85(9):1125-1128, 1996.*

Cant et al. Egg and Cows' milk hypersensitivity in exclusively breast fed infants with eczema, and detection of egg protein in breast milk. British Medical Journal 291:932-935, 1985.*

Weaver et al. Human milk IgA concentrations during the first year of lactation. Arch. Dis. Chil. 78:235-239, 1998.*

Karlsson et al. 'Allergen-responsive CD4 CD25 Regulatory T Cells in Children who Have Outgrown Cow's Milk Allergy.' J. Exp. Med. 199(12):1679-1688. 2004.*

El-Loly et al. 'Bovine Milk Immunoglobulins in Relation to Human Health.' Inter. J. Dairy Sci. 2(3): 183-195, 2007.*

Kelly, C.P. "Immune response to Clostridium difficile infection", European Journal of Gastroenterology and Hepatology, 1996, vol. 8, No. 11, pp. 1048-1053.*

Mulligan, M.E., et al. Elevated levels of serum immunoglobulins in assymptomatic carriers of Clostridium difficile. Clinical Infectious Diseases. vol. 16, Suppl. 4, pp. S239-244, 1993.*

Alfred E. Bacon III et el., Immunoglobulin G Directed Against Toxins A and B of Clostridium Difficile in The General Population And Patients With Antibiotic-Associated Diarrhea; 1994; pp. 205-209, DIAGN Microbiol Infect Dis.

L.A. Barroso et al.: Nucleotide Sequence of Clostridium Difficile Toxin B Gene; Nucleic Acids Research, vol. 18, No. 13; 1990; Oxford University Press.

Jay A: Berzofsky; et al., Antigen-Antibody Interactions and Monoclonal Antibodies; Fundamental Immunology, Third Edition; 1993; pp. 421, 455-464; Raven Press Ltd., New York.

Mary Boesman-Finkelstein, et al.; Bovine Lactogenic Immunity Against Cholera Toxin-Related Enterotoxins and Vibrio Cholerae Outer Membranes; Infection And Immunity; 1989; pp. 1227-1234; American Society for Microbiology.

Harald Brussow et al., Bovine Milk Immunoglobulins For Passive Immunity to Infantile Rotavirus Gastroenteritis; Journal of Clinical Microbiology, Jun. 1987; pp. 982-986; American Society for Microbiology.

Lawrence A. Cone, MD et al., A Durable Responce To Relapsing Clostridium Difficile Colitis May Require Combined Therapy with High-dose Oral Vancomycin and Intravenous Immune Globulin; Infections Diseases in Clinical Practice; vol. 4, No. 4, 2007; pp. 217-220.

B. Corthesy; Recombinant Secretory IGA For Immunle Intervention Against Mucosal Pathogens; Immunoglobulins and Mechanisms of Mucosal Immunity; Biochem Soc Trans; 1997; 471-475.

G. Corthier et al.; Emergence in Gnotobiotic Mics of Nontoxinogenic Clones of Clostridium Difficile from a Toxinogenic One; Infection and Immunity, Jun. 1988; pp. 1500-1504; vol. 56, No. 6.

G. Corthier et al.; Protection Against Experimental Pseudomembranous Colitis in Gnotobiotic Mice by Use of Monoclonal Antibodies Against Clostridium Difficile Toxin A; Infection and Immunity, Mar. 1991, pp. 1192-1195; vol. 59; No. 3.

Pascal Crottet et al; Expression, Purification and Biochemical Characterization of Recombinant Murine Secretory Component: A Novel Tool in Mucosal Immunology; Biochem Society J; 1999; pp. 299-306.

C. H. Dove et al.; Molecular Characterization of the Clostridium Difficile Toxin A Gene; Infection and Immunity; Feb. 1930. pp. 480-488; vol. 56, No. 2.

Marion Ehrich et al.; Production of Clostridium Difficile Antitoxin: Infection and Immunity, Jun. 1980; pp. 1041-1043: vol. 28, No. 3.

Ronald Fayer et al.; Immunotherapeutic Efficacy of Bovine Colostral Immunoglobulins from a Hyperimmunized Cow against Cryptosporidiosis in Neonatal Mice; Infection and Immunity, Sep. 1990: pp. 2962-2965; vol. 58, No. 9.

Dale N. Gerding; Clostridium Difficile-Associated Diarrhea and Colitis in Adults; A Prospective Case-Controlled Epidemilogic Study; Arch Intern Med; vol. 146, Jan. 1986.

Helmut Hilpert et al ; Use of Bovine Mild Concentrate Containing Antibody to Rotavirus to Treat Rotavirus Gastroenteritis in Infants; The Journal of Infectious Diseases; vol. 156, No. 1; Jul. 1987; pp. 158-166.

Robert M.L. Jones et al.; Thiol-Disulfide Redox Buffers Maintain a Structure of Immunoglobulin A that is Essential For Optimal in Vitro Binding to Secretory Component; Biochimica et Biophysica; 1998; pp. 265-274.

Ciaran P. Kelly et al; Clostridium Difficiie Colitis; NEJM—Clostridium Difficile Colitis; pp. 1-17, 1994.

Ciaran P. Kelly et al.; Human Colonic Apirates Containing Immunoglobulin A Antibody to Clostridium Difficile Toxin A Inhibit Toxin A-Receptor Binding; 1992; The American Gastroenterological Association; pp. 35-40.

Donald Y.M. Leung et al; Treatment with Intravenously Administered Gamma Globulin of Chronic Relapsing Colitis Induced by Clostridium Difficile Toxin: From the Division of Pediatric Allergy-Immunology; pp. 633-637, J. Pediatr 118:633-637, 1991.

Jeffrey M. Libby et al; Effects of the Two Toxins of Clostridium Difficile in Antibiotic-Associated Cecitis in Hamsters; Infection and Immunity; May 1982; pp. 822-829.

Aldo A.M. Lima et al.; Effects of Clostridium Difficile Toxins A and B in Rabbit Small and Large Intestine in Vivo and on Cultured Cells In Vitro; Infection and Immunity; Mar. 1988: pp. 582-588; vol. 56, No. 3.

Thomas J. Louie et al.; Tolevamer, a Novel Nonantibiotic Polymer, Compared with Vancomycin in the Treatment of Mild to Moderately Sever Clostridium Difficile-Associated Diarrhea; Clinical Infections Diseases; 2006; pp. 411-420.

Elke Lullau et al; Antigen Binding Properties of Purified Immunoglobulin A and Reconstituted Secretory Immunoglobulin A Antibodies; The Journal of Biological Chemistry, pp. 16300-16309, 1996.

David M. Lyerly et al.; Clostridium Difficile: Its Disease and Toxins; Clinical Microbloiogy Review; Jan. 1988, pp. 1-18.

David M. Lyerly et al.; Characterization of Toxins A and B of Clostridium Difficile with Monoclonal Antibodies; Infection and Immunity, Oct. 1986: pp. 70-76; vol. 54, No. 1.

David M. Lyerly et al.; Passive Immunization of Hamsters against Disease Caused by Clostridium Difficile by Use of Bovine Immunoglobulin G Concentrate; Infection and Immunity, Jun. 1991; pp. 2215-2218; vol. 59, No. 6.

D.M. Lyerly et al ; Biological Activities of Toxins A and B of Clostridium Difficile; Infection and Immunity Mar. 1982; pp. 1147-1150.

David M. Lyerly et al.; Effects of Clostridium Difficle Toxins Given Intragastrically to Animals; Infection And Immunity Feb. 1985; pp. 349-352: vol. 47; No. 2.

S. Mahe et al; Effect of Various Diets on Toxin Production by Two Strains of Clostridium Difficile in Gnotobiotic Mice; Infection And Immunity, Aug. 1987; pp. 1801-1805; vol. 55, No. 8.

Ramon D. Martinez et al.; Purification and Charcterization of Clostridium Sordellii Hemorrhagic Toxin and Cross-Reactivity with Clostridium Difficile Toxin A (Enterotoxin) Infection and Immunity; May 1988, pp. 1215-1221, vol. 56, No. 5.

Lynne V. McFarland et al.; Nosocomial Acquistiori of Clostridium Difficile infection; The New England Journal of Medicine; pp. 204-210, 1989.

Lynne V. McFarland et al; Review of Clostridium Difficile-Associate Disease; American Journal of Infection Control; vol. 14, No. 3, Jun. 1986; pp. 99-109.

(56) References Cited

OTHER PUBLICATIONS

Stuart McPherson et al; Intravenous Immunoglobulin for the Treatment of Severe, Refractory, and Recurrent Clostridium Difficile Diarrhea; Disease of the Colon & Rectum; The American Socity of Colon and Rectal Surgeons; pp. 640-645, 2006.

C. Mietens et al; Treatment of Infantile *E. coli* Gastroenteritis With Specific Bovine Anti-*E. coli* Milk Immunoglobulins; European Journal of Pediatrics; 1979; pp. 239-252.

T. J. Mitchell et al; Effect of Toxin A and B of Clostridium Difficile on Rabbit Ileum and Colon; Gut, 1986; pp. 78-85.

Charalabos Pothoulakis et al; Characterization of Rabbit Ileal Receptors for Clostridium Difficile Toxin A; Evidence For A Receptor-Coupled G Protein; Ileal Receptor for Toxin A; pp. 119-125, 1991.

Sara W. Rothman et al: Differenlial Cytotoxic Effects of Toxins A and B Isolated From Clostridium Difficile; Infection and Immunity; Nov. 1984: pp. 324-331.

Jindrich Symersky et al; Expression of the Recombinant Human Immunoglobulin J Chain In *Escherichia coli*; 2000; Molecular Immunology; pp. 133-140.

Carol. O. Tacket et al; Protection By Milk Immunoglobulin Concentrate Against Oral Challenge With Enterotoxigenic *Eschericia Coli*; the New England Journal of Medicine; May 1988; pp. 1240-1243.

J. Salcedo et al; Intravenous Immunoglobulin Therapy For Sever Clostridium Difficile Colitis; gut.bmj.com; Dec. 2006, pp. 366-370.

Kenneth D. Tucker et al; Toxin A of Clostridium Difficile Is A Potent Cytotoxin; Journal of Clinical Microbiology; pp. 869-871, vol. 28, No. 5, 1990.

R. Weltzin et al; Intranasal Monoclonal IGA Antibody to Respiratory Synctial Virus Protects Rhesus Monkeys Against Upper and Lower Respiratory Tract Infection; pp. 256-261.

Richard Weltzin et al; Intranasal Monoclonal Immunoglobulin A Against Respiratory Syncytial Virus Protects Against Upper and Lower Respiratory Tract Infections in Mice; Antimicrobial Agents and Chemotherapy; Dec. 1994; pp. 2785-2791, 1994.

Y. Yoshiyama et al; Specific Antibodies to Cholera Toxin In Rabbit Milk Are Protective Against Vibrio Cholerae-Induced Intestinal Secretion; Immunology; 1987; pp. 543-547.

L.A. Barroso et al; Nucleotide Sepuence of Clostridium Difficile Toxin B Gene; Nucleic Acids Research, vol. 18, No. 13; pp. 4004, 1990.

Stuart Johnson et al; Selective Neutralization of a Bacterial Enterotoxin by Serum Immunoglobulin A in Response to Mucosal Disease; Infection and Immunity; Aug. 1995; pp. 3166-3173; vol. 63; No. 8.

Jon B. Morris et al; Role of Surgery in Antibiotic-Induced Pseudomembranous Enterocolitis: The American Journal of Surgery; vol. 160. Nov. 1990; pp. 535-539.

Hiltrud Stubbe et al; Polymeric IGA Is Superior to Monomeric IGA and IGG Carrying The Same Variable Domain in Preventing Clostridium Difficile Toxin A Damaging of T84 Monolayers; The American Association of Immunologists; 2000, pp. 1952-1960.

Marina S. Morgan et al; 'The Lancet; vol. 341: Mar. 1993; pp. 701, 702, 1036.

George Triadafilopoulos et al; Differential Effects of Clostridium Difficile Toxins A and B on Rabbit Ileum; 1957; vol. 93; The American Gastroenterolocial Association; pp. 273-279.

Mark H. Wilcox; Descriptive Study of Intravenous Immunoglobulin for The Treatment of Recurrent Clostridium Difficile Diarrhoea; Journal of Antimicrobial Chemotherapy; 2004; pp. 882-884.

J.L. Oncley et al; The Separation of the Antibodies, Isoagglutinins, Prothrombin, Plasminogen and B1-Lipoprotein Into Subfractions of Human Plasma; Journal of The American Chemical Society; Feb. 1949; vol. 71; No. 2.

Delacroix, D.L,. et al., "Selective Transport of Polymeric; Immunoglobulin A in Blie", J. Clin Invest., The Andersen Society for Clinical Investigation, Inc., vol. 70, Aug. 1982, pp. 230-241.

Delacroix, D.L., et al., "Changes in Size, Subclass; and Metabolic Properties of Serum Immunoglobulin A in Liver Diseases and in Other Diseases with High Serum Immunoglobulin A", J. Clin, Invest., The American Society for Clinical Investigation, Inc., vol. 71, Feb. 1983, pp. 358-367.

Saturno, E.J. et al., "Oral Immunoglobulin Therapy in a Child with Severe Clostridium Difficile Diarrhea", LSU Health Sciences Center, New Orleans, LA.(1),, J Allergy Clin Immunol, Feb. 2006, S284 Abstracts.

Bouvet, J.P. et al., "Secretory Component-Binding Properties of Normal Serum IgM", Scand.J. Immunol. 31, pp. 437-441, 1990, Paris, France.

Prinsloo, E. et al., "In vitro refolding of recombinant human free secretory component using equilibrium gradient dialysis", Protein Expression & Purification 47 (2006) 179-185.

Carayannopoulos, L., et al., "Immunoglobulins Structure and Function", Fundamental Immunology. Third Edition, New York, 1993, pp. 283-314.

Cohn, E.J. et al., "Preparation and Properties of Serum and Plasma Proteins IV. A System for the Separation into Fractions of the Protein and Lipoprotein Components of Biological Tissues and Fluids", J. Am. Chem. Soc., 1946, pp. 459-475, vol. 68.

Kohler, G. et al., "Continuous cultures of fused cells secreting antibody of predefined specificity", Nature, Aug. 7, 1975, pp. 495-497, vol. 256, © 1975 Macmillan Publishers Ltd.

Harrison, M. et al., "Cows' milk protein intolerance: a possible association with gastroenteritis, lactose intolerance, and IgA deficiency", British Medical Journal, Jun. 19, 1976, pp. 1501-1504, vol. 1.

Granato, D.A. et al., "A mouse monoclonal IgE antibody anti bovine milk beta-lactoglobulin allows studies of allergy in the gastrointestinal tract", Clin. exp. Immunol., 1986, pp. 703-710, vol. 63.

Karlsen, A. et al., "A novel affinity purification method to isolate peptide specific antibodies", Journal of Immunological Methods, 1990, pp. 151-157, vol. 128, © 1990 Elsevier Science Publishers B.V. (Biomedical Division).

Tjellstrom, B. et al., "Oral immunoglobulin A supplement in treatment of Clostridium difficile enteritis", The Lancet, Mar. 13, 1993, pp. 701-702, vol. 341.

Walker, A.M. et al., "Features of transient hypogammaglobulinaemia in infants screened for immunological abnormalities", Archives of Disease in Childhood, 1994, pp. 183-186, vol. 70.

Cicalese, L. et al., "Decreased Mucosal IgA Levels in Ileum of Patients with Chronic Ulcerative Colitis", Digestive Diseases and Sciences, Apr. 1995, pp. 805-811, vol. 40, No. 4, © 1995 Plenum Publishing Corporation.

Leibl, H. et al., "Method for the isolation of biologically active monomeric immunoglobulin A from a plasma fraction", Journal of Chromatography B: Biomedical Applications, 1996, pp. 173-180, vol. 678, ©1996 Elsevier Science B.V.

Chaves-Olarte, E. et al., "Toxins A and B from Clostridium difficile Differ with Respect to Enzymatic Potencies, Cellular Substrate Specificities, and Surface Binding to Cultured Cells", J. Clin. Invest., Oct. 1997, pp. 1734-1741, vol. 100, No. 7, © 1997 The American Society for Clinical Investigation, Inc.

Borriello, S.P., "Pathogenesis of Clostridium difficile infection", Journal of Antimicrobial Chemotherapy, 1998, pp. 13-19, vol. 41, Suppl. C, © 1998 The British Society for Antimicrobial Chemotherapy.

Kabir, S., "Jacalin: a jackfruit (*Artocarpus heterophyllus*) seed-derived lectin of versatile applications in immunobiological research", Journal of Immunological Methods, 1998, pp. 193-211, vol. 212, © 1998 Elsevier Science B.V.

Schwarze, J. et al., "Antigen-specific Immunoglobulin-A Prevents Increased Airway Responsiveness and Lung Eosinophilia after Airway Challenge in Sensitized Mice", Am. J. Resp. Crit. Care Med., 1998, pp. 519-525, vol. 158.

Shimoda, M. et al., "Local Antibody Response in Peyer's Patches to the Orally Administered Dietary Protein Antigen", Biosci. Biotechnol. Biochem., 1999, pp. 2123-2129, vol. 63, No. 12.

Frossard, C.P. et al., "Antigen-specific secretory IgA antibodies in the gut are decreased in a mouse model of food allergy", J. Allergy Clin. Immunol., Aug. 2004, pp. 377-382, vol. 114, © 2004 American Academy of Allergy, Asthma and Immunology; DOI: 10.1016/j.jaci.2004.03.040.

(56) References Cited

OTHER PUBLICATIONS

Marietta, E. et al., "A new model for dermatitis herpetiformis that uses HLA-DQ8 transgenic NOD mice", The Journal of Clinical Investigation, Oct. 2004, pp. 1090-1097, vol. 114, No. 8; DOI: 10.1172/JCI200421055.

Trajkovski, V. et al., "Plasma Concentration of Immunoglobulin Classes and Subclasses in Children with Autism in the Republic of Macedonia: Retrospective Study", Croatian Medical Journal, 2004, pp. 746-749, vol. 45, No. 6.

Yang, P-C et al., "A murine model of ulcerative colitis: induced with sinusitis-derived superantigen and food allergen", BMC Gastroenterology, Mar. 3, 2005, pp. 1-11, vol. 5, No. 6, © 2005 Yang et al.; DOI: 10.1186/1471-230X-5-6.

Bartlett, J.G. et al., "Treatment of Clostridium difficile-Associated Disease (CDAD)", Medical Letter, Apr. 2007, pp. 993-995, vol. 109, No. 4 (Originally published in The Medical Letter, Nov. 6, 2006, pp. 89-90, vol. 48, No. 1247), © 2006 American College of Obstetricians and Gynecologists.

Babcock, G.J. et al., "Human Monoclonal Antibodies Directed against Toxins A and B Prevent Clostridium difficile-Induced Mortality in Hamsters", Infection and Immunity, Nov. 2006 (Published ahead of print on Sep. 11, 2006), pp. 6339-6347, vol. 74, No. 11, © 2006 American Society for Microbiology.

Hata, T. et al., "Rapid single-tube method for small-scale affinity purification of polyclonal antibodies using HaloTag (TM) Technology", Journal of Biochemical and Biophysical Methods, 2007, pp. 679-682, vol. 70, © 2007 Elsevier B.V.; DOI: 10.1016/j.jbbm.2007.01.014.

Vighi, G. et al., "Allergy and the gastrointestinal system", Clinical and Experimental Immunology, The Journal of Translational Immunology, 2008, pp. 3-6, vol. 153, Suppl. 1, © 2008 The Authors, Journal compilation, © 2008 British Society for Immunology, Clinical and Experimental Immunology; DOI: 10.1111/j.1365-2249.2008.03713.x.

Jyonouchi, H., "Non-IgE Mediated Food Allergy", Inflammation & Allergy—Drug Targets, 2008, pp. 173-180, vol. 7, No. 3, © 2008 Bentham Science Publishers Ltd.

Matysiak-Budnik, T. et al., "Secretory IgA mediates retrotranscytosis of intact gliadin peptides via the transferrin receptor in celiac disease", The Journal of Experimental Medicine, Jan. 21, 2008 (Published online: Dec. 31, 2007), pp. 143-154, vol. 205, No. 1, © 2008 The Rockefeller University Press; DOI: 10.1084/jem.20071204.

Vojdani, A., "Detection of IgE, IgG, IgA and IgM antibodies against raw and processed food antigens", Nutrition & Metabolism, May 12, 2009, pp. 1-17, vol. 6, No. 22, © 2009 Vojdani; DOI: 10.1186/1743-7075-6-22.

Wang, M. et al., "Peanut-induced intestinal allergy is mediated through a mast cell-IgE-FceRI-IL-13 pathway", J. Allergy Clin. Immunol., Aug. 2010 (Available online: Jul. 12, 2010), pp. 306-316, vol. 126, No. 2, © 2010 American Academy of Allergy, Asthma & Immunology; DOI: 10.1016/j.jaci.2010.05.017.

Possin, M.E. et al., "The Relationships Among Immunoglobulin Levels, Allergic Sensitization and Viral Respiratory Illnesses in Early Childhood", Pediatr. Allergy Immunol., Author manuscript available in PMC in Sep. 1, 2011, Published in final edited form as: Pediatr. Allergy Immunol., Sep. 2010, pp. 990-996, vol. 21, No. 6.

Caubet, J-C. et al., "Current understanding of the immune mechanisms of food protein-induced enterocolitis syndrome", Expert Rev. Clin. Immunol., 2011, pp. 317-327, vol. 7, No. 3, © 2011 Expert Reviews Ltd.; DOI: 10.1586/ECI.11.13.

\* cited by examiner

TREATMENT OF CELIAC DISEASE, C. DIFFICILE INFECTION, FOOD INTOLERANCE AND FOOD ALLERGY WITH SECRETORY IGA/IGM

CROSS REFERENCE TO RELATED APPLICATIONS

This application is a continuation of U.S. patent application Ser. No. 15/014,200 filed Feb. 3, 2016, now U.S. Pat. No. 9,409,996, which in turn is a continuation of U.S. patent application Ser. No. 14/264,053 filed Apr. 28, 2014, now U.S. Pat. No. 9,273,129, which in turn is a continuation of U.S. patent application Ser. No. 13/214,952 filed Aug. 22, 2011, now U.S. Pat. No. 8,709,413, that in turn is a continuation-in-part of U.S. patent application Ser. No. 12/138,758 filed Jun. 13, 2008, now U.S. Pat. No. 8,021,645; which in turn is a continuation-in-part of U.S. patent application Ser. No. 11/851,606 filed Sep. 7, 2007, now U.S. Pat. No. 7,794,721; which in turn is a continuation-in-part of U.S. patent application Ser. No. 11/839,781 filed Aug. 16, 2007, now U.S. Pat. No. 7,597,891; which in turn is a continuation-in-part of U.S. patent application Ser. No. 11/610,154 filed Dec. 13, 2006. The contents of these applications are hereby incorporated by reference.

FIELD OF THE INVENTION

This invention relates in general to processess for the treatment of celiac disease, *Clostridium difficile* associated diseases such as *Clostridium difficile* colitis, pseudomembranous colitis and antibiotic associated diarrhea, food intolerance, and food allergy with orally administered immunoglobulin A (IgA), including secretory IgA or secretory IgM, compositions administered in the form of pharmaceutical compositions.

BACKGROUND OF THE INVENTION

Food intolerance includes, but is not limited to, food protein enteropathy and food protein enterocolitis/proctitis (G. Vighi, et al 2008, Caubet et al 2011). Irritatable bowel syndrome is sometimes caused by food intolerance.
The symptoms of irritable bowel syndrome can vary significantly from person to person. A partial listing of irritable bowel syndrome symptoms includes:
  Abdominal pain
  Abdominal distention, bloating, gas, indigestion
  Constipation
  Diarrhea, chronic or occasional
Food allergy is most often attributed to IgE antibodies with antigenic specificity for specific foods (Granato and Piguet 1986; Wang et al 2010). Foods normally induce local intestinal mucosal production of IgA and IgM (Shimoda et al 1999). Food intolerance and allergy are associated with deficiency in IgA (Walker et al 1999, Harrison et al 1976). It has been hypothesized that food antigen IgA may competitively bind to food antigens, and thereby protect the subject from reacting to that food with an allergic response (Possin et al 2010). Food antigen specific IgA is found in the blood plasma (Vojdani 2009, Trajkovski 2008). Food allergy is associated with a relative decrease in food antigen specific IgA in the intestines (Frossard C P at al 2004). Application of antigen-specific IgA to the respiratory mucosa in mice prevents increased airway hyperreactivity in allergic asthma (Schwarze et al 1998; U.S. Pat. No. 5,670,626). Ulcerative colitis is a chronic inflammation of the large intestine. There is decreased mucosal IgA in the intestinal mucosa of patients with ulcerative colitis (Cicalese et al 1995). Food antigen challenge in the presence of Staphylococcal enteroxin B has been shown to induce ulcerative colitis in a mouse disease model (Yang 2005). Non-IgE mediated food intolerance is also known to exist and be most common in infants and young children due to ingested dietary proteins such as those found in cow's milk and soy protein creating profound discomfort. While non-IgE mediated food allergy is rarely life threatening, it can cause significant morbidity in rapidly growing infants and young children. (Jyonouchi, 2008).

Celiac disease is an inherited, autoimmune disease in which the lining of the small intestine is damaged from eating gluten and other proteins found in wheat, barley, rye, and possibly oats. The symptoms of celiac disease can vary significantly from person to person. This is part of the reason the diagnosis is frequently delayed. For example, one person may have constipation, a second may have diarrhea, and a third may have no irregularity in stools. An endoscopy with enteroscopy, particularly of the distal small intestine which most commonly affected, reveals flattening of the villi.

Celiac disease is an enteropathy resulting from an abnormal immune response to gluten-derived peptides in genetically susceptible individuals. This immune response is initiated by intestinal transport of intact peptide 31-49 and 33-mer gliadin peptides. The transferrin receptor, CD71, is responsible for apical to basal retrotranscytosis of gliadin peptides. During this process peptide 31-49 and 33-mer peptides are protected from degradation. In patients with active celiac disease, CD71 is overexpressed in the intestinal epithelium and colocalizes with immunoglobulin (Ig) A. Intestinal transport of intact peptide 31-49 and 33-mer peptides is blocked by polymeric and secretory IgA. This retrotranscytosis of secretory IgA-gliadin complexes may promote the entry of harmful gliadin peptides into the intestinal mucosa. This may then initiate an immune response and perpetuate intestinal inflammation. These findings strongly implicate CD71 in the pathogenesis of celiac disease (Matysiak-Budnik T et al. 2008).

Treatment consists of adherence to a lifelong gluten-free diet. This allows the intestinal villi to heal. Foods, beverages, and medications that contain wheat, barley, and rye are eliminated. Wheat, rye, and barley are the grains that contain pathogenic peptides. Since wheat and barley comprise a major component of the American diet, this diet is difficult to adhere to.

Gastrointestinal symptoms in patients with symptomatic celiac disease who adhere to a gluten-free diet typically resolve within a few weeks. These patients experience the resolution of the findings of malnutrtion, improved growth with resultant normal stature, and normalization of blood and biochemical laboratory studies. Normal results from a follow-up endoscopy with biopsy several months after the diagnosis and treatment confirm the disease.

*Clostridium difficile* (*C. difficile*) is a gram-positive anaerobic bacillus.

Antibiotic associated pseudomembranous colitis results from the use of broad-spectrum antibiotic agents such as clindamycin. These antibiotics cause diarrhea in about 10% of treated patients and pseudomembranous colitis in about 1%. *C. difficile* causes antibiotic associated diarrhea and almost all cases of pseudomembranous colitis.

Pseudomembranous colitis results from the production of *C. difficile* toxin A (MW, 308,000) and toxin B (MW, 270,000) in the colon (Barroso et al., Nucleic Acids Res., 1990; 18:4004; Dove et al., Infect. Immun., 1990; 58:480-488; Lyerly et al., Clin. Microbiol. Rev., 1988; 1:1-18).

Toxin A probably causes most of the gastrointestinal symptoms because of its enterotoxic activity (Lyerly et al., Infect. Immun., 1982; 35:1147-1150; Lyerly et al., Infect. Immun., 1985; 47:349-352). The toxins may act synergistically and the initial pathology caused by toxin A allows toxin B to manifest its toxicity (Lyerly et al., Infect. Immun., 1985; 47:349-352).

Most patients with *C. difficile* associated disease are treated effectively with vancomycin or metronidazole. Other treatment modalities include tolevemer, a toxin binding polymer (T. J. Louie et al., Clin. Infect. Dis. 2006; 43:411), and an antiparasitic medication, nitazoxanide (Med. Letter Drugs Ther. 2006; 48:89). However, relapses occur in about 20-25% of patients. Therefore, there is still a need for additional effective treatment of *Clostridium difficile* associated disease in humans.

Immunological treatment is valuable. Vaccination against toxins A and B stimulates active immunity against *C. difficile* disease in animals (Libby et al., Infect. Immun., 1982; 36:822-829). However, vaccines against the organism and its toxins are not available for human use.

Passive immunization is another immunological treatment. Serum antibodies against *C. difficile* protect hamsters against *C. difficile* disease after oral administration. Passive immunization with bovine antibodies has been proposed as a treatment for other infectious diseases of the gastrointestinal tract, such as diseases caused by rotavirus, enteropathogenic and enterotoxigenic *Escherichia coli*, *Vibrio cholerae*, and *Cryptosporidium parvum*. Preliminary studies indicate that such passive immunization provides protection (Boesman-Finkelstein et al., Infect. Immun., 1989; 57:1227-1234; Brussow et al., J. Clin. Microbiol., 1987; 25:982-986; Fayer et al., Infect. Immun., 1990; 58:2962-2965; Hilpert et al., J. Infect. Dis., 1987; 156:158-166; Mietens et al., Eur. J. Pediatr., 1979; 132:239-252; Tacket et al., N, Engl. J. Med., 1988; 318:1240-1243; Yoshiyama et al., Immunology, 1987; 61:543-547).

It has been reported that bovine immunoglobulin G (IgG) concentrate from the colostrum of cows vaccinated with *C. difficile* toxoid protects hamsters against antibiotic associated cecitis. The hamsters were protected when treated before the onset of diarrhea but not after diarrhea began (Lyerly et al., Infection and Immunity, Vol. 59, No. 6, pages 2215-2218 (1991)). IgG directed against toxins A and B of *C. difficile* are present in the general population (Bacon and Fekety, Diagn. Microbiol. Infect. Dis., 1994; 18:205-209), Human intravenous immunoglobulin derived from plasma donors has facilitated treatment in some patients, especially patients who lack circulating antibodies to the *C. difficile* toxins (Leung D. Y. et al., J. Pediatr. 1991 April; 118(4 (Pt 1)):633-7; Salcedo J. et al., Gut 1997; 41:366-370; Wilcox M. H., J. Antimicrob. Chemoth. 2004; 53:882-884; McPherson S. et al., Dis. Colon Rectum 2006; 49:640-645; Cone L. A. et al., Infect. Dis. Clin. Pract. 2006; 14:217-220).

In vitro experiments have demonstrated that polymeric immunoglobulin is superior to monomeric immunoglobulin in preventing *C. difficile* toxin damage to intestinal epithelial cell monolayers (Stubbe H. et al., J. Immunol. 2000; 164: 1952-1960).

Administration of an immunoglobulin product containing specific antibodies to *C. difficile* results in the elimination of *C. difficile* toxins and also killing of the bacteria within the colon as detailed in U.S. Pat. No. 5,773,000. Such passive immunization therefore provides an effective approach for the treatment of *C. difficile* associated diseases such as colitis, pseudomembranous colitis and antibiotic associated diarrhea. This is especially important for patients experiencing multiple relapses.

Current treatments for *C. difficile* associated disease use antibiotics such as metronidazole and vancomycin. These drugs result in further disruption of the intestinal flora and are associated with a 20-25% incidence of disease relapse.

Monomeric polyclonal IgA admixed with polyclonal IgG (2:1) was derived from plasma (IgAbulin, Immuno, Vienna) (100 mg/mL). Four mL was administered orally 3 times daily for 3 weeks to a three and one-half year old child with antibiotic-associated diarrhea and *C. difficile* toxin A in his stools. Vancomycin administration was continued concurrently. The child improved on this treatment (Tjellstrom B. et al., Lancet 1993; 341:701702). Polyclonal IgG derived from pooled plasma was administered to a second child with refractory *C. difficile* diarrhea who had failed treatment with antibiotics and intravenous polyclonal IgG. This patient received oral polyclonal IgG at 200 mg/kg/day every 2 days for 3 doses together with courses of oral vancomycin and Lactobacillus. The child had recovered at follow-up evaluation 2 weeks later (Saturna E J at al 2006). These reports demonstrate the efficacy of oral passive immunization with pooled immunoglobulins derived from the general population. It appears that monomeric circulatory immunoglobulins possess efficacy. However, increased efficacy is achieved by polymeric secretory IgM owing to the propensity of monomeric circulatory immunoglobulins to degrade in the gastrointestinal tract. The resultant dosing requirements increase treatment costs. The prior art use of circulatory immunoglobulins failed to explore secretory IgM as a potential medicament.

The prior art failed to explore orally administered IgAs or IgMs as a potential medicament for the treatment of celiac dieseae, *Clostridium difficile* associated diseases such as *Clostridium difficile* colitis, pseudomembranous colitis and antibiotic associated diarrhea, food allergy and food intolerance.

Thus, there exists a need for an IgA therapeutic or an IgM therapeutic for the treatment of food allergy and food intolerance. There also exists a need to provide such a therapeutic in a dosing form well suited for treating an affected subject.

SUMMARY OF THE INVENTION

A process is provided for inhibiting symptoms of food allergy or food intolerance in a subject that includes the oral administration of an IgA or an IgM, to the subject suffering from food allergy or food intolerance an IgA or an IgM. When administered in a therapeutic quantity based on the subject characteristics and the type of IgA or IgM, symptoms of food allergy or food intolerance in that subject are inhibited. Even non-secretory forms of IgA and IgM are effective when administered orally. The administered immunoglobulin is readily formed from monoclonal or polyclonal sources. Recombinant forms of the immunoglobulins are also operative herein. When the immunoglobulin is IgA, the IgA is readily administered in a monomeric, dimeric, or polymeric form that optionally includes secretory component. When the. immunoglobulin is IgM, the IgM is readily administered in a monomeric, or pentameric form that optionally includes secretory component.

A composition for treating a subject, especially a human subject, is provided. The composition includes a pentameric or hexameric IgM therapeutic that is formed by combining polyclonal pentameric or hexameric IgM containing J chain with a, recombinant secretory component in a molar ratio of the pentameric or hexameric IgM to the secretory component of 1:1. Formulating agents are mixed with the pentameric or hexameric IgM to yield a dosing form of a capsule, tablet, and a suppository. The IgM therapeutic is optionally enterically coated or microencapsulated to withstand gastrointestinal exposure associated with oral delivery. The dosing form is in a daily amount of between 0.1 and 50 grams. The dosing form containing the IgM therapeutic optionally also includes an antibiotic.

A process for manufacturing a medicament for the treatment of C. difficile associated disease in a, human is also provided that includes the collection of polyclonal pentameric or hexameric IgM as a byproduct of cold ethanol fractionation of pooled plasma derived from more than one human individual. The polyclonal pentameric or hexameric IgM is subjected to antiviral treatment to yield a virus free polyclonal pentameric or hexameric IgM that is also sterilized. The pentameric or hexameric IgM regardless of origin is modified with secretory component to form a secretory pentameric or hexameric IgM therapeutic. The pentameric secretory IgM therapeutic is then mixed with formulating agents to create a capsule, tablet, or suppository dosing form. The pooled plasma is optionally derived from specifically immune or immunized donors. The therapeutic is amenable to enrobement directly through microencapsulation or the dosing form is coated with an enteric coating. A method of treatment for C. difficile with the therapeutic is also provided. The treatment is amenable to supplementation with concurrent or prior antibiotic administration.

DETAILED DESCRIPTION OF THE PREFERRED EMBODIMENTS

The present invention has utility as a treatment for celiac disease, C. difficile infection, food intolerance, irritable bowel syndrome and ulcerative colitis as well as food allergy. The process includes treatment with monoclonal- or polyclonal-IgAs that are monomeric, dimeric or polymeric; and/or monoclonal- or polyclonal-IgM that are monomeric, pentameric and/or secretory. While monomeric IgA is susceptible to gastrointestinal degradation it has been surprisingly found that monomeric immunoglobulin maintains some antibody function after oral administration (Kelly C et al 1997) Because of its resistance to degradation in the gastrointestinal tract, secretory IgA and secretory IgM are generally effective at lower doses. Immunoglobulins have minimal side effects because they are naturally present in the gastrointestinal tract. Dimeric IgA and pentameric IgM according to the present invention may be bound to secretory component in order to mimic secretory IgA and secretory IgM endogenous to the subject. Alternatively they may be administered without bound secretory component.

As used herein, "food allergy" is defined to include IgE and non-IgE mediated allergy and intolerance.

As used herein, a "subject" is defined as a humans.

As the present invention uses an immunoglobulin rather than a metabolic or immunological inhibitor, an effective treatment is provided which does not disturb the body's metabolism.

Allergens that induce food allergies or food intolerance that are mitigated by the present invention illustratively include those allergens found in milk; peanuts; tree nuts, such as cashews and hazelnuts; cauliforates such as cauliflower and broccoli, gluten containing grain crops such as wheat, barley and rye; cheese; eggs; shellfish such as mollusks and crusteaceans; fish; and fruits such as strawberries, bananas, and tomatoes.

The following description of the preferred embodiment(s) is merely exemplary in nature and is in no way intended to limit the invention, its application, or uses.

IgAs and IgMs in various forms including monoclonal- or polyclonal-IgAs that are monomeric, dimeric or polymeric; and monoclonal- or polyclonal-IgMs that are secretory or pentameric are all known to the art, as evidenced for example, by the references incorporated herein.

In one embodiment, the invention provides a process for medical treatment of humans involving the oral administration of secretory IgA which can be derived from a number of sources. One such source for the IgA is pooled human plasma following Cohn cold ethanol fractionation to produce fraction III precipitate as performed by those of skill in the art of protein separation. IgA byproduct is further purified by adsorption onto an ion exchange medium in neutral or slightly acidic conditions as performed by those of skill in the art of protein purification. Another source for the IgA is recombinant IgA produced from a hybridoma or a transgenic plant.

A more detailed description of isolation of an IgA component as a byproduct from pooled human plasma or hyperimmune pooled human plasma is as follows. Ethanol fractionation of pooled human plasma is a well-known process to prepare immunoglobulin G. Pooled human plasma is first obtained from licensed plasmapheresis centers in the United States and tested for various pathogens including the HIV virus. The first manufacturing step of most commercial immunoglobulin G preparations involves a modified cold ethanol fractionation according to Cohn to produce Cohn fraction II. In the fractionation process, many infectious viruses are eliminated from the pooled human plasma. Following fractionation, the Cohn fraction II is subjected to adsorption onto an ion exchange medium. This step may selectively reduce the IgA concentration to less than 0.1%. Such a step is important for producing immunoglobulin G for intravenous infusion into humans. This is because some individuals undergo an anaphylactic-like reaction if treated with intravenous IgG that contains IgA as an impurity.

The modified cold ethanol fractionation process according to Cohn is a series of fractionations using various levels of ethanol, pH, and temperature to produce a fraction II which is further treated to produce immunoglobulins as described above. In the fractionation method, pooled human plasma is first treated to produce a cryoprecipitate and cryo-supernatant. The cryo-supernatant is subjected to a first ethanol fractionation to yield a supernatant I. Supernatant I is subjected to a second ethanol fractionation to yield fraction II+III. Fraction I+III is subjected to a third ethanol fractionation procedure to yield a supernatant III and Fraction III precipitate.

The fraction III precipitate enriched in IgA is generally discarded as an unwanted byproduct. According to the invention, this unwanted IgA following ion exchange adsorption purification is further treated by incubation with immobilized hydrolases to inactivate viruses and vasoactive substances. Such treatment has been proven to eliminate many viruses tested including HIV, Sindbis, and vaccinia. Other antiviral treatments, as known to those skilled in the art, are used in combination and consist of solvent detergent processes, nanofiltration and/or heat inactivation. Usually three antiviral steps are implemented. Following incubation to remove viruses, the concentration of the active material is adjusted with sterile saline or buffered solutions to ensure a constant amount of active material per milliliter of reconstituted product. Finally, the solution with a constant amount of reconstituted product is sterilized by filtration before use.

The ethanol fractionation process according to Cohn is well known in the art and is described in Cohn et al., J. Am. Chem. Soc. 1946; 68:459-475, Oncley et al., J. Am. Chem. Soc. 1949; 71:541-550, and in most detail in pages 576-602, Kirk-Othmer Encyclopedia of Chemical Technology, Vol. 3, second edition (1963). Alternatively, ion exchange chromatography may be used to obtain the dimeric and polymeric IgA byproduct during the manufacture of intravenous immunoglobulin. From 4% to 22% of plasma IgA is dimeric and polymeric IgA (Delacroix et al. 1981; Delacroix et al. 1983). The resulting dimeric and polymeric IgA-J chains are purified.

In a preferred embodiment, the compositions of the invention contain, in addition to the IgA component, recombinant secretory component. Human secretory component can be produced by recombinant techniques as described in Crottet et al., Biochem. J. 1999; 341:299-306. The resulting dimeric IgA is further coupled to recombinant secretory component. In a preferred embodiment, the coupling is accomplished by forming disulfide bonds under mildly oxidizing conditions. (Jones 1998) Dimeric IgA containing both J chain and secretory component is again purified by ion-exchange and size exclusion chromatography and/or ultrafiltration as described in Lullau et al., J. Biol. Chem. 1996; 271:16300-16309, Corthesy, Biochem. Soc. Trans. 1997; 25:471-475, and Crottet et al., Biochem. J. 1999; 341:299-306, as performed by those of skill in the art of protein purification. Purified dimeric and polymeric IgA containing secretory component is optionally stabilized for example by the addition of human serum albumin to a final concentration of 5%. The presence of the human J chains and secretory component in the compositions of the invention leads to doses of immunoglobulin A which are more physiologically effective than compositions without such components.

Dimeric IgA contains two IgA monomers plus J chain.

The present invention has utility as a treatment for C. difficile infections. Unlike prior usage of monomeric IgA and IgG that is susceptible to gastrointestinal degradation, the present invention uses pentameric or hexameric secretory IgM. Because of its resistance to degradation in the gastrointestinal tract, it can be used at lower doses. Pentameric or hexameric IgM according to the present invention are bound to secretory component in order to mimic secretory IgA and IgM endogenous to the subject.

The present invention is superior to polymeric immunoglobulins administered orally because of the presence of secretory component protects the IgM from digestion in the gastrointestinal tract. Polyclonal immunoglobulins, including polyclonal pentameric and hexameric IgM, directed against toxins A and B of C. difficile are present in the general population and are currently discarded as an unwanted by-product of the manufacture of intravenous immunoglobulin. The present invention affords a prophylactic or active treatment of C. difficile disease alone, or in conjunction with a synergistic antibiotic. Current treatment of C. difficile associated disease is plagued by an unacceptable failure rate and antibiotic retreatment of patients with C. difficile associated disease results in the acquisition of additional unwanted antibiotic resistance.

As the present invention uses an immunoglobulin rather than antibiotics, an effective treatment is provided which does not disturb the intestinal flora.

In one embodiment, the invention provides a method for medical treatment of humans involving the oral administration of a secretory IgM component which can be derived from a number of sources. One such source for the IgM is pooled human plasma following Cohn cold ethanol fractionation to produce fraction IgM precipitate as performed by those of skill in the art of protein separation. IgM byproduct is further purified by adsorption onto an ion exchange medium in neutral or slightly acidic conditions as performed by those of skill in the art of protein purification.

A more detailed description of isolation of an IgM component as a byproduct from pooled human plasma or hyperimmune pooled human plasma is as follows. Ethanol fractionation of pooled human plasma is a well-known process to prepare immunoglobulin G. Pooled human plasma is first obtained from licensed plasmapheresis centers in the United States and tested for various pathogens including the HIV virus. The first manufacturing step of most commercial immunoglobulin G preparations involves a modified cold ethanol fractionation according to Cohn to produce Cohn fraction II. In the fractionation process, many infectious viruses are eliminated from the pooled human plasma. Following fractionation, the Cohn fraction II is subjected to adsorption onto an ion exchange medium. This step may significantly selectively reduce the IgA and IgM concentrations. Such a step is important for producing immunoglobulin G for intravenous infusion into humans. This is because some individuals undergo an anaphylactic-like reactions if treated with intravenous IgG that contains IgA or IgM (which may activate complement) as an impurity.

The modified cold ethanol fractionation process according to Cohn is a series of fractionations using various levels of ethanol, pH, and temperature to produce a, fraction II which is further treated to produce immunoglobulins as described above. In the fractionation method, pooled human plasma is first treated to produce a cryoprecipitate and cryo-supernatant. The cryo-supernatant is subjected to a first ethanol fractionation to yield a supernatant I. Supernatant I is subjected to a second ethanol fractionation to yield fraction II+III. Fraction II+III is subjected to a third ethanol fractionation procedure to yield a supernatant III and Fraction III precipitate.

The fraction III precipitate enriched in IgM is generally discarded as an unwanted byproduct. According to the invention, this unwanted IgM following ion exchange adsorption purification is further treated by incubation with immobilized hydrolases to inactivate viruses and vasoactive substances. Such treatment has been proven to eliminate many viruses tested including HIV, Sindbis, and vaccinia. Other antiviral treatments, as known to those skilled in the art, are used in combination and consist of solvent detergent processes, nanofiltration and/or heat inactivation. Usually three antiviral steps are implemented. Following incubation to remove viruses, the concentration of the active material is adjusted with sterile saline or buffered solutions to ensure a constant amount of active material per milliliter of reconstituted product. Finally, the solution with a constant amount of reconstituted product is sterilized by filtration before use.

The ethanol fractionation process according to Cohn is well known in the art and is described in Cohn et al., J. Am. Chem. Soc. 1946; 68:459-475, Oncley et al., J. Am. Chem. Soc. 1949; 71:541-550, and in most detail in pages 576-602, Kirk-Othmer Encyclopedia of Chemical Technology, Vol. 3, second edition (1963). Alternatively, ion exchange chromatography may be used to obtain the pentameric and hexameric IgM byproduct during the manufacture of intravenous immunoglobulin. From 5% to 10% of plasma IgM is pentameric and hexameric IgM (Carayannopoulos and Capra 1993). The resulting pentameric and hexameric IgM-J chains are purified.

In a preferred embodiment, the compositions of the invention contain, in addition to the IgM component, recombinant secretory component. Human secretory component can be produced by recombinant techniques as described in Crottet et al., Biochem. J. 1999; 341:299-306. The resulting pentameric and hexameric IgM is further coupled to recombinant secretory component as known to those skilled in the art (Bouvet J-P at al 1990; Prinsloo E at al 2006). Pentameric IgM containing both J chain and secretory component is again purified by ion-exchange and size exclusion chromatography and/or ultrafiltration as performed by those of skill in the art of protein purification. Purified pentameric and hexameric IgM containing secretory component is optionally stabilized for example by the addition of human serum albumin to a final concentration of 5%. The presence of the human J chains and secretory component in the compositions of the invention leads to doses of immunoglobulin M which are more physiologically effective than compositions without such components.

In another embodiment, a pentameric and hexameric IgM containing component is isolated as a byproduct from hyperimmune pooled human plasma for coupling with secretory component. Hyperimmune pooled human plasma is obtained from donors who have been immunized against a specific disease or are immune to the disease following natural infection. Pentameric and hexameric IgM contains 5, or 6, IgM monomers per J chain, respectively.

In another embodiment, the IgM composition contains a monoclonal antigen-specific IgM (United States Patent Application 20070154469 Irie; Reiko Jul. 5, 2007); the IgM component is further combined with recombinant secretory component to produce a more physiologically effective composition.

The secretory IgM antibodies may be administered alone as a liquid or solid, preferably in a solid powder form and preferably in admixture with a carrier to form a pharmaceutical composition such as a tablet, capsule or suppository.

The secretory IgA antibodies may be administered alone as a liquid or solid, preferably in a solid powder form and preferably in admixture with a carrier to form a pharmaceutical composition such as a tablet, capsule or suppository.

Since preferred methods of administration are oral with solid oral dosage forms such as tablets and capsules being especially preferred, or enteric installation. These are prepared according to conventional methods known those skilled in the art. The secretory IgA antibodies may also be combined with other pharmaceutically acceptable carriers such as various liquids, proteins or oils which may also provide additional nutritional and/or pharmaceutical benefits. Remington Science and Practice of Pharmacy, $20^{th}$ ed. (2000).

These compositions optionally contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged residence in the intestinal lumen of the IgA or IgM can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art; as detailed, for example in U.S. Pat. Nos. 4,017,647; 4,385,078; 4,518,433; and 4,556,552.

They may contain opacifying agents, and can also be of such composition that they release the active compound or compounds in a certain part of the intestinal tract in a delayed manner. Examples of embedding compositions which can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Since the effect of the IgA and IgM antibodies is dependent on their reaching the small intestine, preferred tablets or capsules are enteric coated. Alternatively, the active IgA and IgM antibodies can themselves be microencapsulated prior to formulation. Preparation of microcapsules of IgA and IgM antibody as well as preparation of enteric coated tablets or capsules can be achieved by conventional methods as detailed above.

It is appreciated that the therapeutic amount of IgA or IgM depends on the form thereof, with forms subject to gastrointestinal degradation requiring larger doses. Typically amounts of IgA or IgM from about 0.005 mg to 50 grams per day are used and preferably, 1 mg to 40 grams per day. Generally, secretory IgA or IgM are each independently effective as a treatment when provided to the patient at about 1 gram per day. Forms of IgA or IgM that are prone to gastrointestinal degradation are typically effective in doses increased by at least 80% relative to secretory forms. For example, about 5 grams of secretory IgA could be given to a subject per day in a single dose or in divided doses 3 to 4 times per day. Preferably, multiple doses are administered with meals likely containing food allergens. It is appreciated that a physician can readily adjust the doses of the IgA or IgM to be administered based on the subject's response to treatment. Many factors are considered in dose adjustments. Dosages of secretory IgA or secretory IgM for adult humans envisioned by the present invention and considered to be therapeutically effective will range from between about 5 mg to 50 g. However, it is to be understood that doses can readily be adjusted to provide appropriate amounts of the IgA antibody to any subject, including children.

The present invention also provides a process for medical treatment of humans involving the oral administration of monomeric IgA which can be derived from pooled human plasma or monoclonal IgA which can be derived by hybridoma technology (B Cell Design, Limoge, France).

The present invention also provides a process for medical treatment of humans involving the oral administration of secretory IgM which can be derived from pooled human plasma following Cohn cold ethanol fractionation to produce fraction III precipitate as performed by those of skill in the art of protein separation as described above. IgM byproduct is further purified by adsorption onto an ion exchange medium in neutral or slightly acidic conditions as performed by those of skill in the art of protein purification. Another source for the IgM is recombinant IgM produced from a hybridoma.

The invention is further described by reference to the following detailed examples, wherein the processologies are as described below. These examples are not meant to limit the scope of the invention that has been set forth in the foregoing description. Variations within the concepts of the invention are apparent to those skilled in the art.

Example 1

Monoclonal monomeric IgA is obtained from hybridoma technology. The monoclonal IgA is stabilized by the addition of human serum albumin to a final concentration of 5% and encapsulated. The final solution is adjusted to a therapeutic dose of 5 mg IgA daily. The IgA is administered to a person suffering with irritable bowel disease. One day after initiation of treatment, the irritable bowel syndrome sufferer eats the food to which he/she is sensitive without inducing any symptoms of intestinal dysfunction.

Example 2

The monoclonal IgA per Example 1 is administered to a person suffering with food allergy. While receiving treatment the food allergy sufferer eats the allergenic food without inducing any symptoms of an allergic reaction.

Example 3

The process of Example 2 is repeated with the IgA administered with an enteric, encapsulating coating and a lower daily dose of 2 mg to achieve a similar result.

Example 4

The process of Examples 2 is repeated with monoclonal IgA replaced with polyclonal IgA that is obtained from pooled human plasma following Cohn cold ethanol fractionation to produce fraction III precipitate. IgA is further purified by adsorption onto an ion exchange medium in neutral or slightly acidic conditions. IgA-J chain dimers and polymers are purified. IgA-J chain dimers and polymers are then further coupled to recombinant secretory component again by disulfide bonding in mildly oxidizing conditions, preferably at a molar ratio of secretory component to IgA-J chain dimers and polymers of 1:1. IgA containing both J chain and secretory component is again purified. Purified IgA containing J chain and secretory component is stabilized by the addition of human serum albumin to a final concentration of 5%. The final solution of secretory IgA is adjusted to a therapeutic dose of 5 mg IgA and is administered to a person suffering with food allergy to eggs. One month after initiation of treatment the food allergy sufferer eats 50 grams of egg without inducing any symptoms of an allergic reaction.

Example 5

The process of Example 4 is repeated with a person suffering from a food intolerance to cauliforates to achieve a similar result.

Example 6

The process of Example 4 is repeated with a person suffering from ulcerative collitis to achieve a similar result.

Example 7

The process of Example 4 is repeated with a person suffering from a food allergy to strawberries to achieve a similar result.

Example 8

The process of Example 4 is repeated with a person suffering from irritable bowel syndrome to achieve a similar result.

Example 9

The process of Example 4 is repeated with a person suffering from a peanut allergy to achieve a similar result.

Example 10

The process of Example 4 is repeated with monoclonal IgA replaced with polyclonal IgM that is obtained from pooled human plasma following Cohn cold ethanol fractionation to produce fraction III precipitate. IgM is further purified by adsorption onto an ion exchange medium in neutral or slightly acidic conditions. IgM-J chain pentamers are purified. IgM-J chain pentamers are then further coupled to recombinant secretory component again by disulfide bonding in mildly oxidizing conditions, preferably at a molar ratio of secretory component to IgM-J chain pentamers of 1:1. IgA containing both J chain and secretory component is again purified. Purified IgM containing J chain and secretory component is stabilized by the addition of human serum albumin to a final concentration of 5%. The final solution is adjusted to a therapeutic dose of 10 mg IgM. The IgM is administered to a person suffering with food allergy. One month after to initiation of treatment the food allergy sufferer eats the allergenic food without inducing any allergic symptoms.

Examples 10-14

Examples 5-9 are repeated with monoclonal IgA replaced with polyclonal IgM per Example 10 to achieve like results.

Example 15

Polyclonal IgM is obtained from pooled human plasma following Cohn cold ethanol fractionation to produce fraction III precipitate. IgM is further purified by adsorption onto an ion exchange medium in neutral or slightly acidic conditions. IgM-J chain pentamers and hexamers are purified. IgM-J chain pentamers and hexamers are then further coupled to recombinant secretory component again by disulfide bonding in mildly oxidizing conditions, preferably at a molar ratio of secretory component to IGM-J chain pentamers and hexamer of 1:1. IgM containing both J chain and secretory component is again purified. Purified IgM containing J chain and secretory component is stabilized by the addition of human serum albumin to a final concentration of 5%. The final solution is adjusted to a therapeutic dose of 5 mg IgM.

An ELISA assay will be used to confirm that the IgM preparation contains specific anti-C. difficile IgM.

ELISA Method

Human secretory IgM levels to C. difficile is measured by ELISA using a modification of the method previously described (C. P. Kelly et al., Gastroenterology 1992; 102: 3540; D. Y. M. Leung et al., J. Pediatr. 1991; 118:633-637 and Bacon and Fekety. Diagn. Microbiol. Infect. Dis. 1994; 18:205-209). Coating antigens used to measure IgM titers included purified C. difficile toxin A and purified C. difficile toxin.

Toxigenic Clostridium difficile is cultured for 72 hours in brain heart infusion broth (Beckton Dickinson, Cockeysville, Md.). The conditioned medium is centrifuged and the supernatant filter sterilized by passage through a 45 um filter (Nalgene). C. difficile toxins A and B are purified from the broth culture supernatant as previously described (C. Pothoulakis et al., J. Clin. Invest. 1991; 88:119-125).

Microtiter plates (Immulon II, Dynatech) are coated with C. difficile toxin A or toxin B (each at 10 μg protein per ml in carbonate buffer pH 9.6, 100 μl per well) by incubation for 2 hours at 37° C. followed by overnight incubation at 4° C. Plates are washed between each incubation step using phosphate buffered saline with 0.05% Tween 20 (PBS-T). Plates are then blocked with 2% human serum albumin (ICN, 100 μl/well) in PBS and incubated for 1 hour at room temperature.

All assays are performed in triplicate.

Horseradish peroxidase-labeled goat anti-human IgM (catalog number STAR98P, AbD Serotec) is used as the secondary antibody (0.2 ug/ml in PBS with 2% human serum albumin) incubated for one hour at 37° C. TMB microwell peroxidase substrate (KPL Laboratories) is used as substrate (100 μl/well) and stopped after 2 to 5 minutes with an equal volume of 1 M phosphoric acid. The optical density is then read at 450 nm with 630 nm as reference using an automated photometer (Dynatech). Controls include substitution of the secondary antibody with peroxidase labeled anti-murine IgM and omission of the peroxidase substrate solution. Results are expressed at the mean optical density of test wells minus mean optical density of background wells (coated with human serum albumin alone).

Example 16

To demonstrate that secretory IgM is capable of inhibiting the enterotoxic effects of C. difficile toxins.

Enterotoxicity Method

Fasting male Wistar rats are anesthetized by intraperitoneal injection of sodium pentobarbital. Laparotomy is performed, the renal pedicles tied and 3H-mannitol (10 μCi, PerkinElmer Life Sciences, Boston, Mass.) administered intravenously. Closed ileal loops (5 cm) are then formed and injected with 400 μl of 50 mM Tris buffer (pH 7.4) or with Tris buffer containing C. difficile culture filtrate (20 ug of protein). The inhibitory effect of secretory IgM is assessed by the addition of secretory IgM (200 ug) to the toxins prior to injection into the ileal lumen.

The abdominal incision is closed and anesthesia maintained with sodium pentobarbital. The animals are sacrificed after 4 hours and the ileal loops immediately harvested. Loop weight to length ratio is determined as a, measure of enterotoxin effect. Mannitol excretion, indicating intestinal permeability, is measured by counting radioactivity in the luminal fluid. Heal tissue samples are also fixed in formalin, paraffin-embedded and sections stained with hematoxylin and eosin. The histologic severity of enteritis is graded taking into account the following features: i) neutrophil margination and tissue infiltration, ii) hemorrhagic congestion and edema of the mucosa, iii) epithelial cell damage. A score of 0 to 3 denotes increasingly severe pathological changes.

Example 17 Treatment of a Person III with C. difficile Associated Disease with Secretory IgM An adult individual ill with C. difficile associated disease is treated with secretory IgM containing antibody activity against C. difficile toxin. Treatment is with 1 gram orally three times daily together with vancomycin in appropriate dosage. Treatment is continued until symptoms resolve and the stool becomes negative for C. difficile toxin.

REFERENCES

Bacon A. E. 3rd, Fekety R. Immunoglobulin G directed against toxins A and B of Clostridium difficile in the general population and patients with antibiotic-associated diarrhea. Diagn. Microbiol. Infect. Dis. 1994; 18:205-209.

Barroso L. A., Wang S. Z., Phelps C. J., Johnson J. L., Wilkins T. D. Nucleotide sequence of Clostridium difficile toxin B gene. Nucleic Acids Res. 1990; 18:4004.

Berzofsky J. A., Berkower I. J., Epstein S. L., Monoclonal Antibodies in Chapter 12, Antigen-Antibody Interactions and Monoclonal Antibodies, pp. 455-465 in Fundamental Immunology, Third Edition, W. E. Paul (ed), Raven Press, N Y 1993. Berzofsky et al., Fundamental Immunology, Third Edition, 1993, pp 455-462.

Boesman-Finkelstein M., Walton N. E., Finkelstein R. A. Bovine lactogenic immunity against cholera toxin-related enterotoxins and *Vibrio cholerae* outer membranes. Infect. Immun. 1989; 57:1227-1234.

Bouvet J P, Pillot J, Iscaki S. Secretory component-binding properties of normal serum IgM. Scand J Immunol. 1990; 31:437-441.

Brussow H., Hilpert H., Walther I., Sidoti J., Mietens C., Bachmann P. Bovine milk immunoglobulins for passive immunity to infantile rotavirus gastroenteritis. J. Clin. Microbiol. 1987; 25:982-986, Carayannopoulos L., Capra J. D. Chapter 9 Immunoglobulins Structure and Function pp. 283-314 in Fundamental Immunology, Third Edition, W. E. Paul (ed), Raven Press, N Y 1993.

Caubet J C, Nowak-Węgrzyn A. Current understanding of the immune mechanisms of food protein-induced enterocolitis syndrome. Expert Rev Clin Immunol. 2011 May; 7(3):317-27.

Cicalese L, Duerr R H, Nalesnik M A, Heeckt P F, Lee K K, Schraut W H, Decreased mucosal IgA levelsin ileumof patients with chronic ulcerative colitis. Dig Dis Sci. 1995 April; 40(4):805-11.

Cohn E. J., Strong L. E., Hughes W. L., Jr., Mulford D. J., Ashworth J. N., Melin M., Taylor H. L., Preparation and Properties of Serum and Plasma Proteins IV. A System for the Separation into Fractions of the Protein and Lipoprotein Components of Biological Tissues and Fluids, J. Am. Chem. Soc. 1946; 68; 459-475.

Cone L. A., Lopez C., Tarleton H. L., Jodoin D., Taylor M., Gade-Andavolu R., Dreisbach L. P. A durable response to relapsing *Clostridium difficile* colitis may require combined therapy with high-dose oral vancomycin and intravenous immune globulin. Infect. Dis, Clin. Pract. 2006; 14:217-220.

Corthesy B., Recombinant Secretory IgA for Immune Intervention Against Mucosal Pathogens, Biochem. Soc. Trans. 1997, 25; 471-475.

Corthier et al., Emergence in Gnotobiotic Mice of Nontoxinogenic Clones of *Clostridium dificile* from a Toxinogenic One, Infection and Immunity, June 1988, pp. 1500-1504.

Corthier et al., Protection Against Experimental Pseudomembranous Colitis in Gnotobiotic Mice by Use of Monoclonal Antibodies Against *Clostridium difficile* Toxin A, Infection and Immunity, March 1991, pp. 1192-1195.

Crottet P., Cottet S., Corthesy B., Expression, Purification and Biochemical Characterization of Recombinant Murine Secretoiy Component, A Novel Tool in Mucosal Immunology, Biochem. J. 1999, 341; 299-306.

Delacroix D. L., Hodgson H. J., McPherson A., Dive C., Vaerman J. P. Selective transport of polymeric immunoglobulin A in bile. Quantitative relationships of monomeric and polymeric immunoglobulin A, immunoglobulin M, and other proteins in serum, bile, and saliva. J. Clin. Invest. 1982 August; 70(2):230-41

Delacroix D. L., Elkom K. B., Geubel A. P., Hodgson H. F., Dive C., Vaerman J. P. Changes in size, subclass, and metabolic properties of serum immunoglobulin A in liver diseases and in other diseases with high serum immunoglobulin A. J. Clin. Invest. 1983 February; 71(2):358-67.

Dove C. H., Wang S. Z., Price S. B., Phelps C. J., Lyerly D. M., Wilkins T. D. and Johnson J. L.; Lyerly et al. Molecular characterization of the *Clostridium difficile* toxin A gene. Infect. Immun. 1990; 58:480-488.

Ehrich et al., Production of *Clostridium difficile* Antitoxin, Infection and Immunity, June, 1980, pp. 1041-1043.

Fayer R., Guidry A., Blagburn B. L. Immunotherapeutic efficacy of bovine colostral immunoglobulins from a hyperimmunized cow against cryptosporidiosis in neonatal mice. Infect. Immun., 1990; 58:2962-2965.

Frossard C P, Hauser C, Eigenmann P A. Antigen-specific secretory IgA antibodies in the gut are decreased in a mouse model of food allergy. J Allergy Clin Immunol. 2004 August; 114(2):377-82.

Granato D A, Piguet P F. A mouse monoclonal IgE antibody anti bovine milk beta-lactoglobulin allows studies of allergy in the gastrointestinal tract. Clin Exp Immunol. 1986 March; 63(3):703-10.

Gerding et al., *Clostridium difficile*-Associated Diarrhea Archives of Internal Medicine, vol. 146, January 1986, pp. 95-100.

Harrison M, Kilby A, Walker-Smith J A, France N E, Wood C B. Cows' milk protein intolerance: a possible association with gastroenteritis, lactose intolerance, and IgA deficiency. Br Med J. 1976 Jun. 19; 1(6024):1501-4.

Harumi Jyonouchi. Non-IgE Mediated Food Allergy. *Inflammation & Allergy—Drug Targets,* 2008, 7, 000-000.

Hilpert H., Brussow H., Mietens C., Sidoti J., Lerner L., Werchau H. Use of bovine milk concentrate containing antibody to rotavirus to treat rotavirus gastroenteritis in infants. J. Infect. Dis. 1987; 156:158-166.

Jones R. M. L., Schweikart F., Frutiger S., Jaton J-C., Hughes G. J. Thiol-disulfide redox buffers maintain a structure of immunoglobulin A that is essential for optimal in vitro binding to secretory component. Biochimica et Biophysica Acta 1998; 1429:265-274.

Kelly C P, Chetham S, Keates S, Bostwick E F, Roush A M, Castagliuolo I, LaMont J T, Pothoulakis C. Survival of Anti-*Clostridium difficile* Bovine Immunoglobulin Concentrate in the Human Gastrointestinal Tract. Antimicrob Agents Chemother. 1997 February; 41(2):236-41.

Kelly et al., *Clostridium difficile* Colitis, New England Journal of Medicine, vol. 330, January 1994, pp. 257-262.

Kelly et al., Human Colonic Aspirates Containing Immunoglobulin A Antibody to *Clostridium difficile* Toxin A Inhibit Toxin A-Receptor Binding, Gastroenterology, vol. 102, No. 1, pp. 35-40.

Kohler G., Milstein C., Continuous Cultures of Fused Cells Secreting Antibody of Predetermined Specificity, Nature 1975; 256; 495-497.

Leung D. Y., Kelly C. P., Boguniewicz M., Pothoulakis C., LaMont J. T., Flores A. Treatment with intravenously administered gamma globulin of chronic relapsing colitis induced by *Clostridium difficile* toxin. J. Pediatr. 1991 April; 118(4 (Pt 1)):633-637.

Libby J. M., Jortner B. S., Wilkins T. D. Effects of the two toxins of *Clostridium difficile* in antibiotic-associated cecitis in hamsters. Infect. Immun. 1982 May; 36(2):822-829.

Lima et al., Effects of *Clostridium difficile* Toxins A and B in Rabbit Small and Large Intestine In Vivo and on Cultured Cells In Vitro, Infection and Immunity, March 1988, pp. 582-588.

Louie T. J., Peppe J., Watt C. K., Johnson D., Mohammed R., Dow G., Weiss K., Simon S., John J. F. Jr., Garber G., Chasan-Taber S., Davidson D. M.; Tolevamer Study Investigator Group. Tolevamer, a novel nonantibiotic polymer, compared with vancomycin in the treatment of mild to moderately severe *Clostridium difficile*-associated diarrhea. Clin, Infect. Dis. 2006; 43:411-20.

Lullau E., Heyse S., Vogel H., Marison I., von Stockar U., Kraehanbuhl J-P., Corthesy B., Antigen Binding Properties of Purified Immunoglulin A Antibodies, J. Biol. Chem. 1996; 271:16300-16309.

Lyerly D. M., Krivan H. C., Wilkins T. D. *Clostridium difficile*: its disease and toxins. Clin. Microbiol. Rev. 1988; 1:1-18.

Lyerly D. M., Phelps C. J., Toth J., Wilkins T. D. Characterization of toxins A and B of *Clostridium difficile* with monoclonal antibodies. Infect. Immun. 1986; 54:70-76.

Lyerly D. M., Bostwick E. F., Binion S. B., Wilkins T. D. Passive immunization of hamsters against disease caused by *Clostridium difficile* by use of bovine immunoglobulin G concentrate. Infect. Immun. 1991; 59:2215-2218.

Lyerly D. M., Lockwood D. E., Richardson S. H., Wilkins T. D. Biological activities of toxins A and B of *Clostridium difficile*. Infect. Immun. 1982; 35:1147-1150.

Lyerly D. M., Saum K. E., MacDonald D. K., Wilkins T. D. Effects of *Clostridium difficile* toxins given intragastrically to animals. Infect. Immun. 1985; 47:349-352.

Mahe et al., Effect of Various Diets on Toxin Production by Two Strains of *Clostridium difficile* in Gnotobiotic Mice, Infection and Immunity, August 1987, pp. 1801-1805.

Martinez et al., Purification and Characterization of *Clostridium sordellii* Hemorrhagic Toxin and Cross-Reactivity with *Clostridium difficile* Toxin A (Enterotoxin), Infection and Immunity, May 1988, pp. 12-15-1221.

McFarland et al., Nosocomial Acquisition of *Clostridium difficile* Infection, The New England Journal of Medicine, January 1989, pp. 204-210.
McFarland et al., Review of *Clostridium difficile* Associated Diseases, American Journal of Infection Control, vol. 14, No. 3, June 1986, pp. 99-104.
McPherson S., Rees C. J., Ellis R., Soo S, and Panter S. J. Intravenous Immunoglobulin for the Treatment of Severe, Refractory, and Recurrent *Clostridium difficile* Diarrhea. Diseases of the Colon & Rectum. 2006; 49(5):640-645.
Med. Letter Drugs Ther. 2006; 48:89-90, 92.
Mietens C., Keinhorst H., Hilpert H., Gerber H., Amster H., Pahud J. J. Treatment of infantile *E. coli* gastroenteritis with specific bovine anti-*E. coli* milk immunoglobulins. Eur. J. Pediatr. 1979; 132:239-252.
Mitchell et al., Effect of Toxin A and B of *Clostridium difficile* on Rabbit Ileum and Colon, Gut, 1986, vol. 27, pp. 78-85.
Morris et al., Role of Surgery in Antibiotic-Induced Pseudomembranous Enterocolitis, The American Journal of Surgery, vol. 160, November 1990, pp. 535-539.
Oncley J. L., Melin M., Richert D. A., Cameron J. W., Gross P. M., Jr., The Separation of the Antibodies, Isoagglutinins, Prothrombin, Plasminogen and β1-Lipoprotein into Subfractions of Human Plasma. J. Am. Chem. Soc. 1949; 71:541-550.
Possin M E, Morgan S, DaSilva D F, Tisler C, Pappas T E, Roberg K A, Anderson E, Evans M D, Gangnon R, Lemanske R F, Gem J E. The relationships among immunoglobulin levels, allergic sensitization, and viral respiratory illnesses in early childhood. Pediatr Allergy Immunol 2010: 21: 990-996.
Pothoulakis C., LaMont J. T., Eglow R., Gao N., Rubins J. B., Theoharides T. C., Dickey B. F. Characterization of rabbit ileal receptors for *Clostridium difficile* toxin A. Evidence for a receptor-coupled G protein. J. Clin Invest. 1991; 88:119-25.
Prinsloo E, Oosthuizen V. Muranmoto K, Naude R J. In vitro refolding of recombinant human free secretory component using equilibrium gradient dialysis. Protein Expr Purif. 2006; 47:179-185.
Rothman et al., Differential Cytotoxic Effects of Toxins A and B Isolated from *Clostridium difficile*, Infection and Immunity, November 1984, pp. 324-331.
Salcedo J. et. al. Gut 1997; 41:366-370.
Saturno E. J., Costa H., Sorensen R. Oral Immunoglobulin Therapy in a Child with Severe *Clostridium difficile* Diarrhea. J Allergy Clin Immunol 2006; 117:S284.
Schwarze J, Cieslewicz G, Joetham A, L Sun L K, Sun W N, Chang T W, Hamelmann E, W. Gelfand E W. Antigen-specific Immunoglobulin-A Prevents Increased Airway Responsiveness and Lung Eosinophilia after Airway Challenge in Sensitized Mice. Am J Resp Crit Care Med 1998; 158:519-525.
Shimoda M, Inoue Y, Azuma N, Kanno C. Local antibody response in Peyer's patches to the orally administered dietary protein antigen. Biosci Biotechnol Biochem. 1999 December; 63(12):2123-9.
Strong L. E., Blood Fractionation, pp. 576-602 in vol. 3, Kirk-Othmer Encyclopedia of Chemical Technology. Second Edition, H. F. Mark, J. J. McKetta, D. F. Othmer (eds), Interscience Publishers, N Y 1963, pp. 576-602.
Stubbe H. et al. J. Immunol. 2000; 164:1952-1960.
Symersky J., Novak J., McPherson D. T., DeLucas L., Mestecky J. Expression of the recombinant human immunoglobulin J chain in *Escherichia coli*. Mol. Immunol. 2000; 37:133-140.
Trajkovski V, Ajdinski L, Spiroski M. Plasma concentration of immunoglobulin classes and subclasses in children with autism in the Republic of Macedonia: retrospective study. Croat Med J. 2004 December; 45(6):746-9.
Tacket C. O., Losonsky G., Link H., Hoang Y., Guesry P., Hilpert H., Levine M. M. Protection by milk immunoglobulin concentrate against oral challenge with enterotoxigenic *Escherichia coli*. N. Engl. J. Med. 1988; 318: 1240-3.
Tjellstrom B., Stenhammar L., Eriksson S., Magnusson K. E. Oral immunoglobulin A supplement in treatment of *Clostridium difficile* enteritis. Lancet 1993; 341(8846): 701-702.
Triadafilopoulos et al., Differential Effects of *Clostridium difficile* Toxins A and B on Rabbit Ileum, Gastroenterology, 1987, vol. 93, pp. 273-279.
Tucker et al., Toxin A of *Clostridium difficile* Is a Potent Cytotoxin, Journal of Clinical Microbiology, May 1990, pp. 869-871.
Vighi G, Marcucci F, Sensi L, G. Di Cara G, Frati F. Allergy and the gastrointestinal system. *Clinical and Experimental Immunology,* 153 (Suppl. 1): 3-6, 2008.
Vojdani A. Detection of IgE, IgG, IgA and IgM antibodies against raw and processed food antigens. Nutr Metab (Lond). 2009 May 12; 6:22
Walker A M, Kemp A M, Hill D J, Shelton M J. Features of transient hypogammaglobulinaemia in infants screened for immunological abnormalities. Arch Dis Child. 1994 March; 70(3): 183-186.
Wang M, Takeda K, Shiraishi Y, Okamoto M, Dakharma A, Joetham A, Gelfand E W. Peanut-induced intestinal allergy is mediated through a mast cell-IgE-FcepsilonRI-IL-13 pathway. J Allergy Clin Immunol. 2010 August; 126(2):306-16, 316.e1-12.
Weltzin R., Traina-Dorge V., Soike K., Zhang J. Y., Mack P., Soman G., Drabik G., Monath T. P., Intranasal Monoclonal IgA Antibody against Respiratory Syncytial Virus Protects Rhesus Monkeys against Upper and Lower Respiratory Tract Infection. J. Infect. Dis. 1996; 174:256-261.

Weltzin R., Hsu S. A., Mittler E. S., Georgakopoulas K., Monath T. P., Intranasal Monoclonal Immunoglobulin A against Respiratory Synctial Virus Protects against Upper and Lower Respiratory Tract Infections in Mice. Antimicrob. Agents Chemother. 1994; 38:2785-2791.

Wilcox M. H. J. Antimicrob. Chemoth. 2004; 53:882-884.

Yang P-C, Wang C-S, An Z-Y. A murine model of ulcerative colitis: induced with sinusitis-derived superantigen and food allergen. BMC Gastroenterology 2005, 5:6.

Yoshiyama Y., Brown W. R. Specific antibodies to cholera toxin in rabbit milk are protective against *Vibrio cholerae*-induced intestinal secretion. Immunology. 1987; 61:543-547.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A composition consisting of:
   a mixture of purified secretory IgA and purified secretory IgM;
   optionally with a carrier for oral delivery;
   wherein dimeric and polymeric IgA and pentameric IgM of said mixture are all individually obtained from pooled human plasma or plasma byproduct, and the obtained IgA and the obtained IgM are all individually purified, are all further treated by incubation with affinity tagged recombinant human secretory component and viruses and vasoactive substances are inactivated and are all stabilized by the addition of a stabilizing agent; and
   optionally including at least one of a filler, an adjuvant, or an enteric coating.

2. The composition of claim 1 wherein the pentameric IgM is monoclonal antigen-specific IgM.

3. The composition of claim 1 wherein the carrier is present and form as tablet or a capsule.

4. The composition of claim 1 wherein the filler is present in a gelatin capsule.

5. The composition of claim 1 wherein the adjuvant is present and is one or more of a wetting agent, an emulsifying agent, a suspending agent, or a flavoring.

6. The composition of claim 1 wherein the enteric coating is present.

7. A composition consisting of:
   a mixture of purified secretory IgA and purified secretory IgM;
   a carrier for oral delivery;
   wherein the secretory IgA and the secretory IgM are obtained from polyclonal IgA and polyclonal IgM, respectively, where the polyclonal IgA and polyclonal IgM are obtained from pooled human plasma;
   wherein the polyclonal IgA and the polyclonal IgM are further purified by adsorption onto an ion exchange medium in neutral or slightly acidic conditions;
   wherein IgA-J chain dimers and polymers are purified;
   wherein IgM-J chain pentamers are purified;
   wherein the IgA-J chain dimers and polymers are then further coupled to recombinant secretory component again by disulfide bonding in mildly oxidizing conditions at a molar ratio of secretory component to IgA-J chain dimers and polymers of 1:1;
   wherein the IgM-J chain pentamers are then further coupled to recombinant secretory component again by disulfide bonding in mildly oxidizing conditions at a molar ratio of secretory component to IgM-J chain pentamers of 1:1;
   wherein the IgA containing both J chain and secretory component is again purified;
   wherein the IgM containing both J chain and secretory component is again purified;
   wherein an adjuvant is present and is one or more of a wetting agent, an emulsifying agent, a suspending agent, or a flavoring; and
   optionally including at least one of a filler or an enteric coating.

8. The composition of claim 7 wherein the pentameric IgM is monoclonal antigen-specific IgM.

9. The composition of claim 7 wherein the carrier is present and form as tablet or a capsule.

10. The composition of claim 7 wherein the filler is present in a gelatin capsule.

11. The composition of claim 7 wherein the enteric coating is present.

* * * * *